US012721945B2

(12) United States Patent
Bodner

(10) Patent No.: US 12,721,945 B2
(45) Date of Patent: Sep. 1, 2026

(54) IMPLANTABLE MEDICAL DEVICE FOR CONTROLLED FLUID FLOW DISTRIBUTION AMONG A PLURALITY OF TREATMENT CATHETERS

(71) Applicant: Medtronic, Inc., Minneapolis, MN (US)

(72) Inventor: Jeffrey Bodner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 873 days.

(21) Appl. No.: 17/085,364

(22) Filed: Oct. 30, 2020

(65) Prior Publication Data

US 2022/0133990 A1 May 5, 2022

(51) Int. Cl.
*A61M 5/142* (2006.01)
*A61M 5/162* (2006.01)
*A61M 5/168* (2006.01)

(52) U.S. Cl.
CPC ........ *A61M 5/14276* (2013.01); *A61M 5/162* (2013.01); *A61M 5/16804* (2013.01); *A61M 2005/14284* (2013.01)

(58) Field of Classification Search
CPC .............. A61M 5/14276; A61M 5/162; A61M 5/16804; A61M 2005/14284; A61M 31/002; A61M 39/223; A61M 39/285
See application file for complete search history.

(56) References Cited

U.S. PATENT DOCUMENTS 4,447,224 A * 5/1984 DeCant, Jr. ....... A61M 5/14276 128/DIG. 13
4,573,994 A 3/1986 Fischell et al.
5,176,641 A * 1/1993 Idriss .................... A61M 5/145 604/131
5,217,442 A 6/1993 Davis
5,624,409 A * 4/1997 Seale ................ A61M 5/16809 604/246
6,283,943 B1 9/2001 Dy et al.
(Continued)

FOREIGN PATENT DOCUMENTS

WO WO 2013/052414 A2 4/2013

OTHER PUBLICATIONS

Application and File History for U.S. Appl. No. 16/803,216, filed Feb. 27, 2020. Inventor: Winek.
(Continued)

*Primary Examiner* — Michael J Tsai
*Assistant Examiner* — Justin L Zamory
(74) *Attorney, Agent, or Firm* — Dymera IP, LLC

(57) ABSTRACT

An implantable drug delivery system that includes a drug delivery device configured to deliver a fluid containing one or more pharmaceutical agents to a patient, a plurality of treatment catheters configured to be implanted within the body of a patient and transport the fluid to the two or more treatment sites, and a flow control hub including an inlet connector that fluidically connects to the drug delivery device to receive the fluid, a plurality of outlet connectors that couple to a respective catheter of the plurality of treatment catheters, and one or more flow restrictors that impede the flow of the fluid from the inlet connector to the plurality of outlet connectors to regulate a flow of the fluid through the plurality of treatment catheters under a selected flow distribution.

25 Claims, 7 Drawing Sheets

(56) References Cited

U.S. PATENT DOCUMENTS 6,579,280 B1 6/2003 Kovach et al.
6,805,687 B2 10/2004 Dextradeur et al.
6,962,580 B2 11/2005 Adams et al.
7,044,932 B2 5/2006 Borchard et al.
7,072,802 B2 7/2006 Hartlaub
7,637,897 B2 12/2009 Ginggen
7,942,863 B2 5/2011 Kalpin et al.
8,535,280 B2 9/2013 Rogers et al.
8,721,605 B2 5/2014 Brandt et al.
9,122,785 B2 9/2015 Alme et al.
9,421,325 B2 8/2016 Kalpin
9,590,352 B2 3/2017 Bilbrey et al.
2004/0256584 A1* 12/2004 Zimmerling .......... F16K 31/086 251/7
2005/0054988 A1* 3/2005 Rosenberg ................ F16K 7/17 604/247
2005/0245887 A1* 11/2005 Olsen ................ A61M 25/0043 604/246
2006/0089619 A1 4/2006 Ginggen
2007/0255227 A1 11/2007 Haase
2009/0082758 A1* 3/2009 Gill ................... A61M 5/14276 604/891.1
2009/0306595 A1* 12/2009 Shih ...................... A61F 9/0017 141/2
2013/0116665 A1 5/2013 Humayun et al.
2014/0228765 A1 8/2014 Burke et al.
2017/0043151 A1 2/2017 Bellrichard et al.
2020/0121849 A1 4/2020 Chrisenson et al.
2020/0121850 A1 4/2020 Christenson et al.

OTHER PUBLICATIONS

Extended European Search Report for European Application No. 19202531.0, dated Jan. 27, 2020.

* cited by examiner

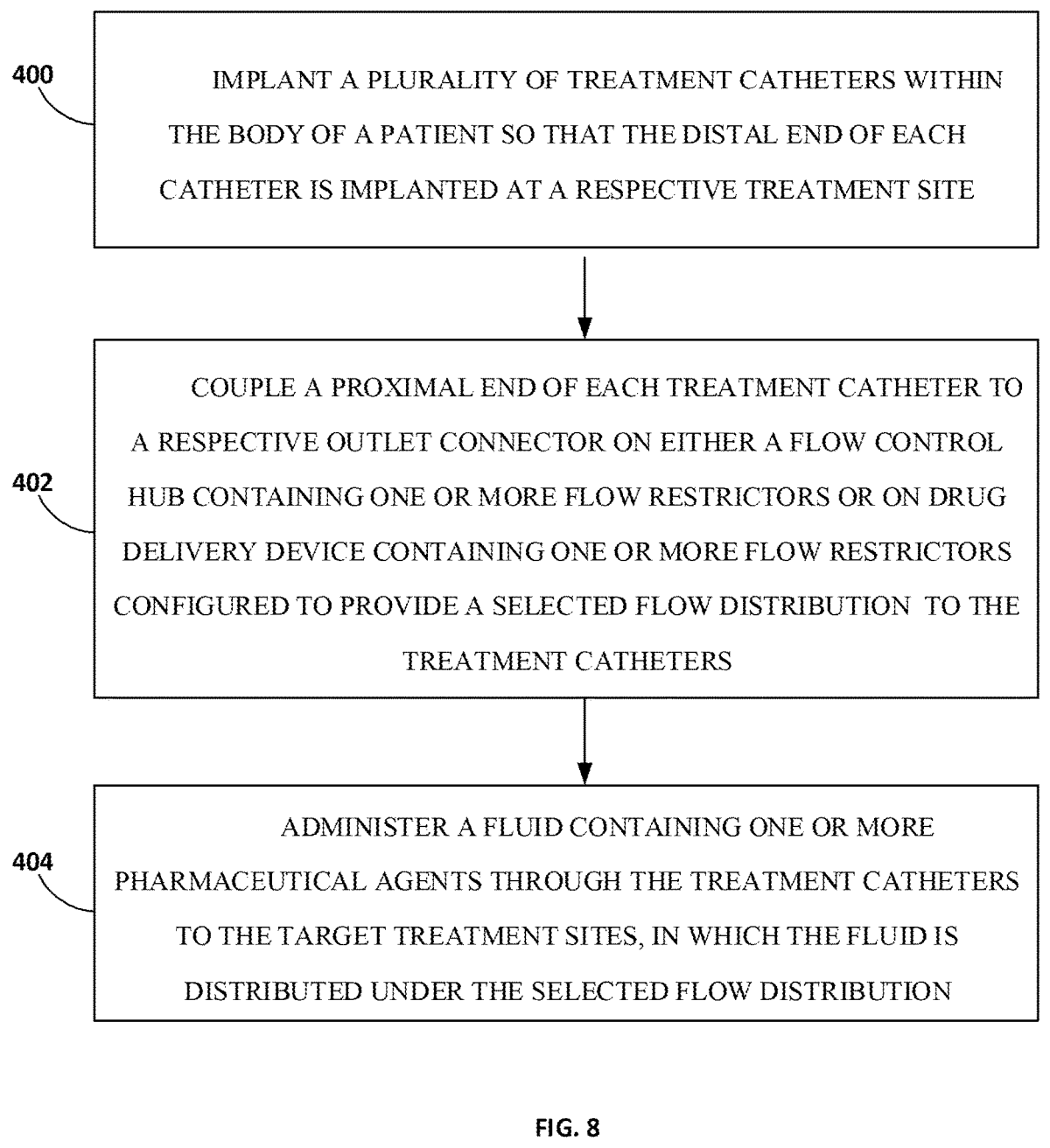

400 — IMPLANT A PLURALITY OF TREATMENT CATHETERS WITHIN THE BODY OF A PATIENT SO THAT THE DISTAL END OF EACH CATHETER IS IMPLANTED AT A RESPECTIVE TREATMENT SITE

402 — COUPLE A PROXIMAL END OF EACH TREATMENT CATHETER TO A RESPECTIVE OUTLET CONNECTOR ON EITHER A FLOW CONTROL HUB CONTAINING ONE OR MORE FLOW RESTRICTORS OR ON DRUG DELIVERY DEVICE CONTAINING ONE OR MORE FLOW RESTRICTORS CONFIGURED TO PROVIDE A SELECTED FLOW DISTRIBUTION TO THE TREATMENT CATHETERS

404 — ADMINISTER A FLUID CONTAINING ONE OR MORE PHARMACEUTICAL AGENTS THROUGH THE TREATMENT CATHETERS TO THE TARGET TREATMENT SITES, IN WHICH THE FLUID IS DISTRIBUTED UNDER THE SELECTED FLOW DISTRIBUTION

FIG. 8

IMPLANTABLE MEDICAL DEVICE FOR CONTROLLED FLUID FLOW DISTRIBUTION AMONG A PLURALITY OF TREATMENT CATHETERS

TECHNICAL FIELD

This invention relates to implantable medical devices, in particular devices containing medical catheters for target specific drug delivery.

BACKGROUND

A variety of medical devices are used for acute, chronic, or long-term delivery of therapy to patients suffering from a variety of conditions, such as chronic pain, tremor, Parkinson's disease, cancer, epilepsy, urinary or fecal incontinence, sexual dysfunction, obesity, spasticity, gastroparesis, and the like. For example, infusion pumps or other fluid delivery devices can be used for chronic delivery of pharmaceutical agents. Typically, such devices provide therapy continuously or periodically according to programmed parameters. The programmed parameters can specify the therapeutic regimen (e.g., the rate, quantity, and timing of medicament delivery to a patient), as well as other functions of the medical device. Additionally, or alternatively, delivery of pharmaceutical agents may be provided by bolus (e.g., periodic) injections aided by the use of infusion pumps that provide access to key positions within a patient's body such as the cerebrospinal fluid.

Such implantable devices often include a treatment catheter for the transport of fluid containing one or more pharmaceutical agents from the location of the implantable drug pump, which are often implanted within a patient's chest, abdomen, or lower back, to the target treatment site. In some embodiments, such devices may be used to transport one or more pharmaceutical agents to two more treatment sites using multiple catheters.

SUMMARY

The present disclosure describes novel devices and techniques for regulating the flow of fluids containing the pharmaceutical agents through the system to provide highly controlled fluid distribution using a single drug pump or port.

In an embodiment, the disclosure describes an implantable drug delivery system configured to deliver one or more pharmaceutical agents to two or more treatment sites within a body of a patient. The system includes a drug delivery device configured to deliver a fluid including the one or more pharmaceutical agents to the patient, a plurality of treatment catheters configured to be implanted within the body of a patient and transport the fluid to the two or more treatment sites, and a flow control hub. The flow control hub includes an inlet connector that fluidically connects to the drug delivery device to receive the fluid, a plurality of outlet connectors that couple to a respective catheter of the plurality of treatment catheters; and one or more flow restrictors that impede the flow of the fluid from the inlet connector to the plurality of outlet connectors to regulate a flow of the fluid through the plurality of treatment catheters under a selected flow distribution.

In another embodiment, an implantable drug delivery system configured to deliver one or more pharmaceutical agents to two or more treatment sites within a body of a patient, the system including a plurality of treatment catheters configured to be implanted within the body of a patient and transport one or more pharmaceuticals agent to two or more treatment sites; and a drug delivery device configured to deliver a fluid having one or more pharmaceutical agents to the patient through the plurality of treatment catheters, the drug delivery device including a drug reservoir for receiving the one or more pharmaceutical agents, a header having a plurality of outlet connectors that each couple to a respective catheter of the plurality of treatment catheters; a pump mechanism configured to pump the fluid comprising the one or more pharmaceutical agents from the drug reservoir through the outlet connectors; and one or more flow restrictors configured to impede the flow of the fluid from the drug reservoir to the plurality of outlet connectors to regulate a flow of the fluid through the plurality of treatment catheters under a selected flow distribution.

In another embodiment, an implantable medical device having a flow control hub including an inlet connector configured to fluidically connect to a drug delivery device that deliver a fluid having one or more pharmaceutical agents to the inlet connector, a plurality of outlet connectors each configured to fluidically connect to a respective treatment catheter, and one or more flow restrictors that impede the flow of the fluid from the inlet connector to the plurality of outlet connectors to regulate a flow of the fluid through the plurality of outlet connectors under a selected flow distribution.

In another embodiment, the disclosure describes a method for treating a medical condition that includes providing an implantable drug delivery system having a drug delivery device including a drug reservoir for receiving a fluid with one or more pharmaceutical agents, a header comprising the plurality of outlet connectors, a pump mechanism configured to pump the fluid comprising the one or more pharmaceutical agents from the drug reservoir through the outlet connectors, and one or more flow restrictors configured to impede the flow of the fluid from the drug reservoir to the plurality of outlet connectors to regulate a flow of the fluid through a plurality of treatment catheters coupled to the plurality of outlet connectors under a selected flow distribution; or a flow control hub comprising an inlet connector that fluidically connects to a drug delivery device to receive a fluid containing one or more pharmaceutical agents, and one or more flow restrictors that impede the flow of the fluid from the inlet connector to a plurality of outlet connectors to regulate a flow of the fluid through a plurality of treatment catheters coupled to the plurality of outlet connectors under a selected flow distribution. The method also includes administering using the drug delivery device, the fluid containing the one or more pharmaceutical agents through a plurality of treatment catheters under the selected flow distribution.

In some embodiments, the disclosed flow restrictors may include a circuitous pathway having a large flow length to width ratio of greater than 10:1. The circuitous pathway flow restrictor may be helical or spiral shaped and provide a five-fold or greater resistance to the flow compared to the theoretical flow resistance of a catheter being coupled distal to the flow restrictor.

The above summary is not intended to describe each illustrated embodiment or every implementation of the subject matter hereof. The figures and the detailed description that follow more particularly exemplify various embodiments.

BRIEF DESCRIPTION OF DRAWINGS

The disclosure can be more completely understood in consideration of the following detailed description of various embodiments of the disclosure, in connection with the accompanying drawings, in which:

FIG. 8 is a flow diagram of a method of implanting and using the drug delivery systems of the present disclosure for the treatment of one or more medical conditions.

Figure 1:
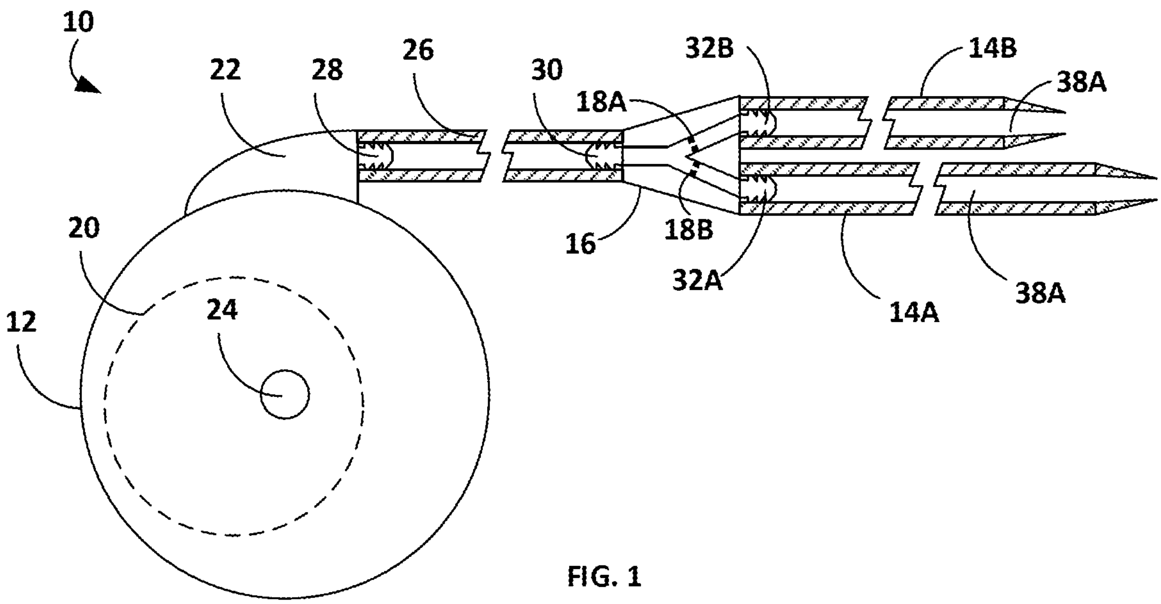
FIG. 1 is a schematic diagram of an implantable drug delivery system in accordance with the disclosure

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

While the concept of using a single implantable drug pump or port to transport one or more pharmaceutical agents to multiple treatments sites has been explored before, practical limitations have hindered the development of such devices. One particular challenge for these devices is obtaining a proper distribution of the pharmaceutical agent to the multiple treatments sites. Natural bends, varying lengths, and the nature of the treatment site can affect the fluid pathway of the catheters leading to unpredictable flow rates and the non-uniform distribution of the fluids containing the pharmaceutical agents at the treatment sites. In some embodiments, the implantable drug pump may be designed with multiple pumps and dedicated lines for the delivery of the pharmaceutical agent to the different treatment sites. However, this approach requires more complex and larger pump hardware and multiple catheter lines. The present disclosure describes novel devices and techniques for regulating the flow of fluids containing the pharmaceutical agents through the system by using one or more flow regulators along the fluid pathway to passively control the distribution of fluid to the different treatment sites to provide highly controlled fluid distribution using a single drug pump or drug port.

FIG. 1 is a schematic diagram of an implantable drug delivery system 10 that includes a drug delivery device 12, a plurality of treatment catheters 14A and 14B, and a flow control hub 16. As described further below, flow control hub 16 includes one or more flow restrictors 18A and 18B configured to impede or restrict the flow of a fluid containing one or more pharmaceutical agents and through the hub to regulate a flow of the fluid through the plurality of treatment catheters 14A and 14B under a selected flow distribution and thereby provide a mechanism for precisely controlling the flow rate through treatment catheters 14A and 14B.

Drug delivery system 10 is configured to be implanted within a patient and hold or receive one or more pharmaceutical agents and deliver such agents to two or more treatment sites via catheters 14A and 14B, which are shown in an enlarged half sections in FIG. 1. The size of catheters 14A and 14B are exaggerated for ease of illustration of the structure thereof and the full length of catheters 14A and 14B are not shown for simplicity of illustration.

Drug delivery device 12 is preferably surgically implanted subcutaneously in the pectoral, abdominal or lower back region of the patient's body and may include any suitable device configured to deliver a fluid containing one or more pharmaceutical agents under a specified regimen scheme (e.g., a set schedule or flow rate). Example drug delivery devices 12 include, but are not limited to, drug infusion pumps or bolus injection ports. For purposes of this disclosure, drug delivery device 12 is generally described as an implantable drug pump, which may include a pumping mechanism and internal processing circuitry and power supply to deliver a fluid containing one or more pharmaceutical agents at a set rate or schedule. However, the concepts may be equally applied to the use of a drug port such as that described in FIG. 4 or other devices.

Examples of some suitable drug pumps may include, e.g., commercially available implantable infusion pumps such as, for example, the SYNCHROMED pumps, such as Models 8611H, EL 8626, and EL 8627, manufactured by Medtronic, Inc., Minneapolis, Minn. It should be understood that some pumps or other delivery devices used in connection with the present disclosure may not require a separate power supply. Drug delivery pumps typically include one or more drug reservoirs 20 that receive one or more pharmaceutical agents and a header 22. Drug reservoir 20 houses the one or more pharmaceutical agents that are delivered via catheters 14A and 14B to the target treatment sites within the body of the patient through header 22 and hub 16.

In some embodiments, drug delivery device 12 may include an access port 24 disposed on an exterior of the housing with a self-sealing septum enabling a needle to access to drug reservoir 20 percutaneously. Port 24 may be used to refill drug reservoir 20 for the purpose of scheduled drug delivery or for the delivery of a bolus injection. The housing of drug delivery device 12 can be constructed of a material that is biocompatible and hermetically sealed, such as titanium, tantalum, stainless steel, plastic, ceramic, or the like to protect the inner workings and components of drug delivery device 12.

Header 22 is fluidically connected to drug reservoir 20 and configured to attach directly or indirectly to inlet connector 30 of flow control hub 16. In FIG. 1, hub 16 is connected to header 22 by intermediate catheter 26 so that the proximal end of intermediate catheter 26 is coupled to outlet connector 28 of header 22, and the distal end of intermediate catheter 26 is coupled to inlet connector 30 of flow control hub 16. In some embodiments, the presence of intermediate catheter 26 may provide the advantage of allowing for the positioning of flow control hub 16 at a separate position within the patient's body than drug delivery device 12 such as closer to the target treatments sites which may allow for greater precision in managing the flow rate through catheters 14A and 14B. For example, positioning flow restrictors 18A and 18B more distally along the fluid flow path of system 10 can provide greater precision and accuracy in managing the fluid distribution and flow between catheters 14A and 14B by reducing the length of the flow path distal to flow restrictors 18A and 18B.

While intermediate catheter 26 is depicted as being a separate and distinct component from flow control hub 16 and drug delivery device 12, in other embodiments, intermediate catheter 26 may be integrally formed with flow control hub 16 or drug delivery device 12 such that flow control hub 16 directly couples to drug delivery device 12. However, having intermediate catheter 26 exist separately and distinct from flow control hub 16 and drug delivery device 12 may help assist with the physician navigating and positioning one or more of drug delivery device 12, intermediate catheter 26, and flow control hub 14 within the patient's body. For example, in examples where drug delivery device 12 and flow control hub 16 are positioned at separate locations within the patient's body, a guide member (e.g., guidewire, guide catheter, or the like) may be used to tunnel and implant intermediate catheter 26. By having intermediate catheter 26 exist as a separate component from flow control hub 16 and drug delivery device 12, the system allows for intermediate catheter 26 to be easily implanted using a guide member and subsequently fluidically connected to both drug delivery device 12 and flow control hub 16 by the physician. Having drug delivery device 12 or flow control hub 16 fused or integrally formed with intermediate catheter 26 may inhibit the use of such guide devices to implant intermediate catheter 26, but may offer greater simplicity in the system.

If included, intermediate catheter 26 may be of any suitable length to provide proper placement of drug delivery device 12 and flow control hub 16 within the patient's body. Further, intermediate catheter 26 may be coupled to flow control hub 16 and drug delivery device 12 using any suitable catheter connector to provide a proper fluid seal. Outlet connector 28 of drug delivery device 12 and inlet connector 30 of flow control hub 16 are depicted as barbed-style connectors in FIG. 1, however other suitable style of connectors may also be used.

Figure 2:
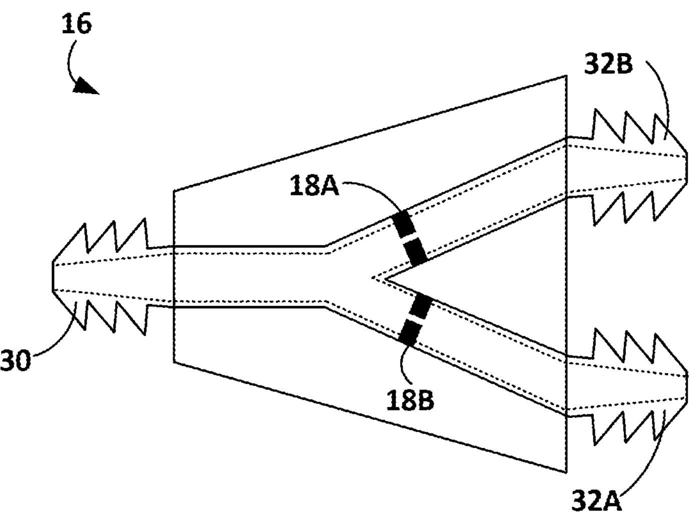
FIG. 2 is a schematic diagram of the flow control hub from the drug delivery system of FIG. 1.

FIG. 2 provides an enlarged view of flow control hub 16 used within drug delivery system 10. As shown, flow control hub 16 includes an inlet connector that fluidically connects to drug delivery device 12 (e.g., via intermediate catheter 26) to receive the fluid containing the one or more pharmaceutical agents. Flow control hub 16 also includes a plurality of outlet connectors 32A and 32B that each couple to a proximal end of a respective catheter of the plurality of catheters 14A and 14B. For ease of illustration, flow control hub 16 is depicted as having only two outlet connectors 32A and 32B which are coupled to catheters 14A and 14B respectively. However, it will be understood by those of ordinary skill in the art that flow control hub 16 can include a plurality of outlet connectors such as two or more, three or more, four or more, and the like depending on the number of different target sites intended to be treated by drug delivery device 12. In such examples, each outlet connector will couple with a respective treatment catheter and the fluid flow path through each outlet connector will be regulated by one or more flow restrictors.

Flow control hub 16 is configured to receive fluid containing one or more pharmaceutical agents from drug delivery device 12 and distribute the fluid into two or more fluid pathways. Flow control hub 14 includes one or more fluid flow restrictors 18A and 18B configured to regulate the fluid distribution to the different fluid pathways by impeding the fluid flow through flow control hub 14 to regulate the flow distribution of the fluid through the plurality of treatment catheters 14A and 14B based on a selected flow distribution. Such impedance may be achieved by using one or more flow restrictors 18A or 18B that substantially restrict or narrow the cross-sectional diameter of the fluid pathway or introduce a substantial pressure drop along the fluid pathway to provide highly controlled flow rates within the different flow pathways.

For example, observations of conventional systems that use a bifurcated catheter (e.g., a catheter that splits fluid flow among two or more distal catheters) have found that the fluid delivered to the different targeted treatment sites may be non-uniform and difficult to predict, even when the system is theoretically balanced. Without being bound by theory, the imbalance of fluid flow in such systems may be due to the different flow impedances within the different fluid pathways. Several factors may affect the flow impedance within the different pathways including, for example, the overall length of the respective treatment catheters, the relative diameters of the catheters, the curvilinear or tortuous flow pathway within the catheters, the dentistry of the target tissue that the fluid is being delivered to, and the like. Each of these factors may alter the flow resistance within the system and lead to imprecise fluid distribution between the treatment catheters. Further, because these factors are primarily a consequence of the implantation, it is not possible to accurately predict the flow distribution prior to implantation.

By including flow restrictors 18A or 18B, the fluid flow is intentionally and substantially restricted, such that the flow restriction introduced by flow restrictors 18A and 18B dominates the system and becomes the controlling feature that manages flow rate through catheters 14A and 14B. Thus, the flow restrictions introduced by the length or tortuous design of catheters 14A and 14B or the relative density of the target treatments sites are effectively negligible in comparison to the flow restriction introduced by flow restrictors 18A and 18B.

In some embodiments, flow restrictors 18A and 18B may each provide at least five times greater restriction to the fluid compared to the theoretical restriction provided by either catheter 14A or 14B, provide at least a seven times greater restriction, or provide at least a 10 times greater restriction. For example, flow restriction through a theoretical catheter may be estimated by Equation 1:

$$R_{cath} = \frac{128\mu \cdot L_{cath}}{\pi \cdot d_{cath}^4} \quad [1]$$

Where $R_{cath}$ is the flow resistance in KPa·s/mL, μ is fluid viscosity which can be assumed to be about $0.7\times10^{-3}$ Pa·s, $L_{cath}$ is the length of the catheter, and $d_{cath}$ is the inner diameter of the catheter. As can be seen, the flow resistance is inversely proportionate to the diameter to the fourth power. Variations in the catheter lengths, kinks in the catheters or varying diameters may cause up to a two-fold difference in the resistances of the two flow paths such that the ratio in the flow resistance of the two catheters 14A and 14B is about 2 (e.g., $R_{cath1}/R_{cath2}=2$).

Including flow resistors in the flow path can greatly reduce the ratio closer to 1 as indicated by Equation 2:

$$\frac{R_{Path1}}{R_{Path1}} = \frac{R_{rest1} + R_{cath1}}{R_{rest2} + R_{cath2}} \quad [2]$$

$R_{rest1}$ and $R_{rest2}$ are the flow resistance through flow restrictors 18A and 18B. As a comparative example, when $R_{rest1}$ and $R_{rest2}$ are equal and approximately five times the flow resistance of $R_{cath1}$, and $R_{cath2}$ is about half the resistance of $R_{cath1}$, the above Equation 2 simplifies to a ratio of less than 1.1 compared to a ratio of 2 if the flow restrictors were not present.

Due to the constrictions introduced by flow restrictors 18A and 18B, a large pressure drop may be achieved in the fluid as the fluid flows through the restrictors. In some embodiments, the pressure drop across each flow restrictor 18A and 18B may be about 2 psi to about 10 psi for a flow rate of about 10 microliters/minute. In comparison, variations in interstitial pressure introduced by the length or tortuous design of catheters 14A and 14B or the relative density of the target treatments sites are typically less than 0.5 psi, and therefore will not create an imbalance of flow in the different treatment catheters 14A and 14B for a desired flow rate of about 1-10 microliters/minute.

Flow restrictors 18A and 18B can be made of any suitable material, including but not limited to, e.g. sintered or porous metals or polymers, capillary tubes, series or orifices, circuitous pathway with large length to width ratio, a material that provides a small diameter fluid path, or other suitable device. Sintered metals may be produced by sintering metal microsphere powders to provide uniform porosity. The metals may include, but are not limited to, light-weight, high tensile strength, and/or radiopaque materials, such as tungsten, titanium or tantalum and sintered using suitable techniques. In embodiments, these metals chosen are largely non-magnetic, and therefore are safe within a magnetic imaging environment.

Additionally, or alternatively, restrictors 18A and 18B may be produced with thin sheet filters (e.g., polyethersulfone or polypropylene, from Pall Corporation (East Hills, N.Y.)), polycarbonate membranes (from Osmonics, Inc. (Minnetonka, Minn.)), polyvinylidine fluoride from Millipore Corporation (Bedford, Mass.)), sintered polyethylene (from Porex Surgical (College Park)), sintered glass (from Robu Glasfilter-Gerate GmbH (Hattert, Germany)), metal chips (e.g., metal orifices such as a sapphire chip or orifice), capillary tubes, or the like.

Orifice-type or "chip" restrictors may be advantageous due to their high sensitivity and correlation between the office diameter and fluid pressure drops. Improvements in manufacturing processes have increased the accuracy and precision in fabricating the orifice diameter allowing for better pairing between two or more such restrictors.

Another type or flow restrictor envisioned is circuitous pathway with large length to width ratio. For example, the restrictor may include a helical passageway (e.g., lumen or channels) coiled around a center axis. Such a structure may resemble of screw-type body having a helical channel cut into an outer surface of a central body. The central body may be sheathed thereby establishing the circuitous pathway with a large length (e.g., the total length of the helical channel) to width (e.g., the cross section of the helical channel perpendicular to the direction of flow). The helix allows for a relatively large flow length in a relatively small volume of space. The desired length and width of such circuitous flow restrictors may be estimated using Equation 1 to provide a desired increase (e.g., 5-fold increase or more) in the flow resistance compared to that of catheters 14A and 14B. Alternative designs for circuitous pathway flow restrictors may include spiral designs that provide long pathways in compact space.

In some embodiments, flow restrictors 18A and 18B may exhibit a theoretical flow resistance that is at least five times greater, at least seven times greater, or at least at least ten times greater than the theoretical flow resistance of the catheter 14A or 14B that the flow restrictor is attached to. Such a relative difference provided by flow restrictors 18A and 18B may ensure that the flow impedance introduced by flow restrictors 18A and 18B dominates the flow pathway.

Flow restrictors 18A and 18B may be appropriately sized using Equations 1, 2, or other techniques to provide a desired flow distribution between catheters 14A and 14B. In some embodiments, equal distribution of flow between catheters 14A and 14B may be desired in which case restrictors 18A and 18B may be substantially the same. In other embodiments, disproportionate drug delivery may be desired between catheters 14A and 14B such as 40:60, 30:70, or 20:80 splits in volumetric flow rate, or the like. Additionally, system 10 may include more than two catheters 14A and 14B each with equal or disproportionate flow distribution.

Flow control hub 16 may be constructed using any suitable material. In some embodiments, the inner fluid pathways and connectors 30, 32A, 32B may be constructed using a semi-rigid polymer such as PEEK, polysulfone, PBS, and the like to ensure integrity of the fluid pathway and proper connection with catheters 14A and 14B and are inert to the therapeutic fluid delivered by the system. The one or more flow restrictors 18A and 18B may be embedded or fused with such polymers during formation. In some embodiments, once the inner fluid pathways are established, the rigid components may be encased in a soft polymer material (e.g., silicone) to provide a soft exterior for patient comfort once implanted.

Catheters 14A and 14B may be of any suitable design to function and transport pharmaceutical agents from drug delivery device 12 to respective distal treatment sites within the patient's body. In preferred embodiments, catheters 14A and 14B are manufactured and provided separately from either drug delivery device 12 or flow control hub 16 and coupled within system 10 after implantation by the physician.

Maintaining separation of catheters 14A and 14B from drug delivery device 12 or flow control hub 16 during implantation may help ease and facilitate proper implantation, particularly compared to existing systems in which a single catheter is bifurcated and therefore cannot be implanted with a guidewire using traditional methods. For example, each catheter 14A and 14B includes an elongated body defining an inner lumen 38A and 38B that provides the fluidic pathway from the proximal end of the catheter to the distal end of the catheter for the delivery of the fluid containing the pharmaceutical agents to the target treatments site.

During implantation, respective guide members may be introduced through the patient's body to the desired treatment sites followed by the advancement of catheters 14A and 14B over or through the guide member to the respective treatment site. With respect to guidewires, catheters 14A and 14B will receive the guidewire within inner lumens 38A and 38B, thereby aiding in their delivery to the target treatment site. With respect to a guide catheter, the catheters 14A and 14B will be advanced through the inner lumen of the guide catheter to the target treatment site.

Once properly implanted, the guide member (e.g., wire or catheter) can be removed from the patient pulling it through inner lumens 38A and 38B or sliding the guide member off the proximal end of the treatment catheter. Having flow control hub 16 connected to one or both of catheters 14A and 14B prior to implantation can inhibit the ability to use a guidewire due to the inclusion of flow restrictors 18A and 18B. Similarly, including flow restrictors 18A and 18B within the body of catheters 14A and 14B will prevent such catheters from being able to receive such guidewires. Further, the relative size of flow control hub 16 would prevent other guide member devices (e.g., guide catheters) from being used to navigate catheters 14A and 14B to the desired treatment sites and allow the guide member to be removed.

By manufacturing flow control hub 16 and catheters 14A and 14B separate and having the physician couple the respective components together after implanting the catheters, allows catheters 14A and 14B to be easily implanted using conventional techniques while also obtaining highly regulated flow pathways. Further, the modular nature of drug delivery system 10 offers additional options for customization and use with commercially available components such as commercially available drug delivery devices 12 or treatment catheters 14A and 14B.

The body of catheters 14A, 14B, and 26 may be constructed of any suitable material, e.g., an elastomeric tube. Examples of some suitable materials include, but are not limited to, silicone rubber (e.g., polydimethyl siloxane) or polyurethane, both of which provide suitable mechanical properties and are very flexible. Suitable materials for catheters 14A, 14B, and 26 are also preferably chemically inert such that the catheters will not interact with drugs or body tissue or body fluids over a long time period.

The inside diameter of the catheters (e.g., the diameter of the lumens 38A and 38B of catheters 14A and 14B) is preferably large enough to accommodate expected infusion rates of the pharmaceutical agent and not compete with the flow resistance introduced by the one or more flow resistors 18A and 18B. As an example, catheters 14A, 14B, and 26 may have an outside diameter of about 1.2 millimeters (mm) to about 2.0 mm and an inside diameter of about 0.4 mm to about 0.6 mm.

Figure 3:
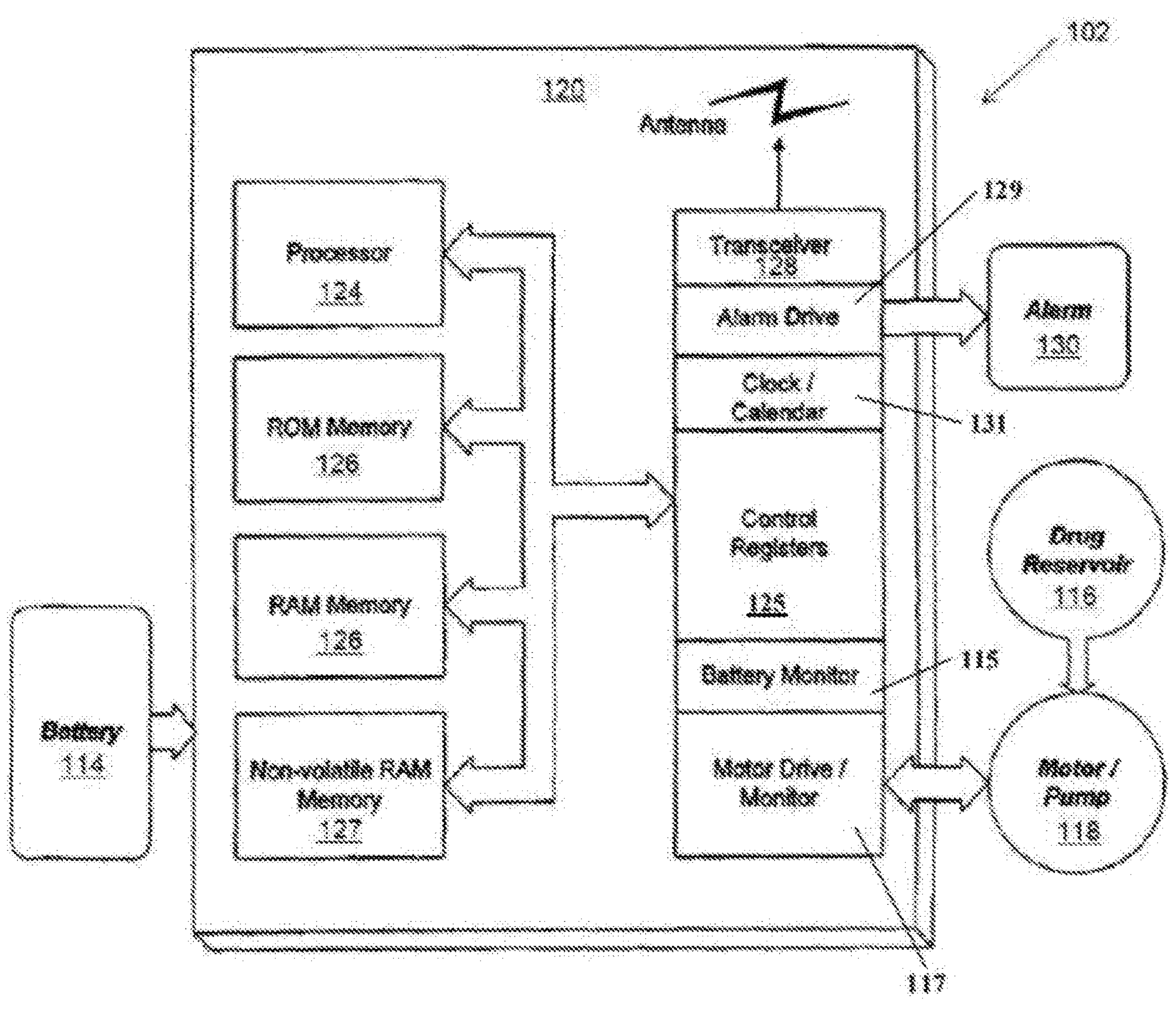
FIG. 3 is a schematic diagram of a drug delivery pump that may be used with the drug delivery system of FIG. 1.

FIG. 3 shows an additional schematic diagram of an example drug delivery device that may be used with drug delivery system 10. The device shown in FIG. 3 includes an implantable drug pump 102 that includes electronic components 120 of the device carried in the housing of device 12 including pump 118 and power source 114.

Power source 114 can be a battery, such as a lithium-ion battery. The power source 114 can be carried in the housing of pump 102 and can operate pump 118 and electronics components 120. A battery monitoring device 115 can monitor a battery power of the battery 114 and a motor drive monitor 117 can monitor operation of pump motor 118.

The electronic components 120 can include a processor 124, RAM or Non-volatile RAM memory 126 and 127, and transceiver circuitry 128 that can interface with one or more control registers 125. In one embodiment, the processor 124 can be an Application-Specific Integrated Circuit (ASIC) state machine, gate array, controller, microprocessor, CPU, or the like. The electronic components 120 can be generally configured to control infusion of medicament according to programmed parameters or a specified treatment protocol. The programmed parameters or specified treatment protocol can be stored in memory 126 or 127. Transceiver circuitry 128 can be configured to receive information from and transmit information to an external programmer or server. In one embodiment, electronic components 120 can be further be configured to operate a number of other features, such as, for example, a patient alarm 130 operable with an internal clock and/or calendar 131 and an alarm drive 129.

Implantable drug pump 102 can be configured to receive programmed parameters and other updates from the external programmer which can communicate with implantable drug pump 102 through well-known techniques such as wireless telemetry. In some embodiments, the external programmer can be configured for exclusive communication with one or more implantable drug pumps 102. In other embodiments, the external programmer can be any computing platform, such as a mobile phone or tablet. In some embodiments, implantable drug pump 102 and an external programmer can further be in communication with a cloud-based server. The server can be configured to receive, store and transmit information, such as program parameters, treatment protocols, drug libraries, and patient information, as well as to receive and store data recorded by implantable drug pump 102. In some embodiments, pump 102 may provide tactile feedback to the user of the location of a needle as described in this disclosure.

Figure 4:
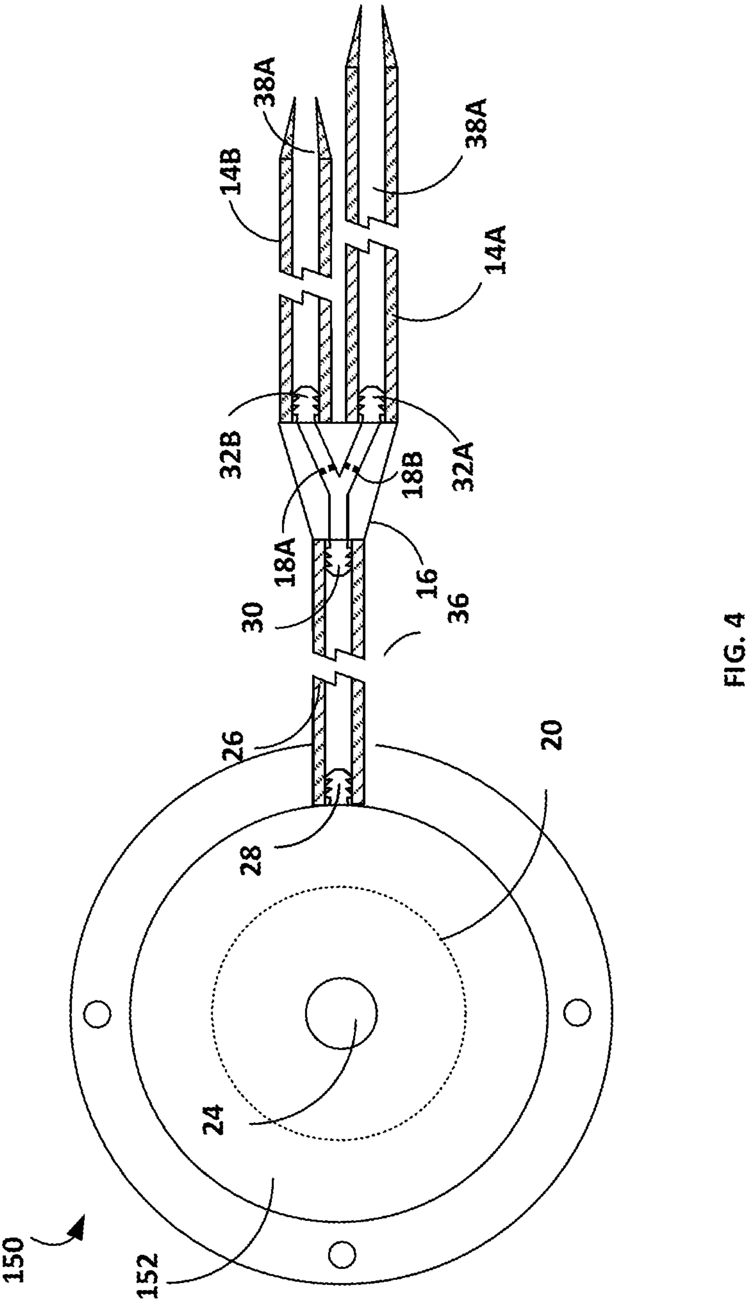
FIG. 4 is a schematic diagram of a drug port that may be used with the drug delivery system of FIG. 1.

FIG. 4 shows another example drug delivery device that may be used with drug delivery system 10. The device shown in FIG. 4 includes an implantable drug port 150 that includes a housing 152 that encloses a port reservoir 21 that is fluidically connected to outlet connector 28. Port reservoir 21 is accessible by access port 24 disposed on an exterior of housing 152 with a self-sealing septum enabling a needle to access to reservoir 21. The housing, reservoir, and access port may be substantially similar to the component described above.

Figure 5:
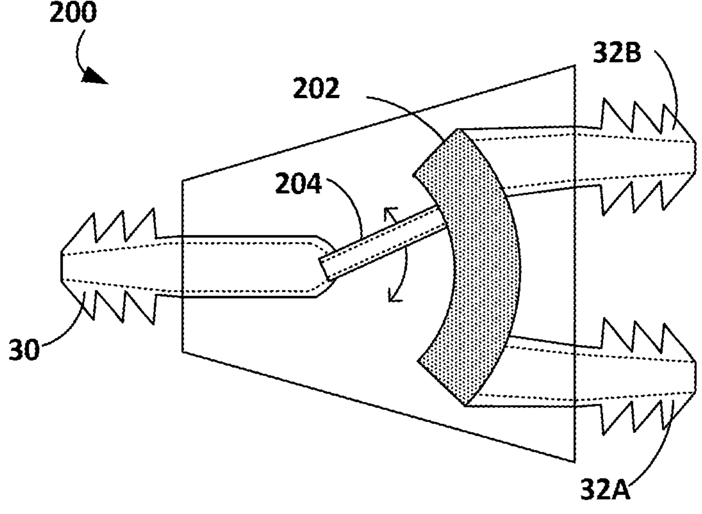
FIG. 5 is a schematic diagram of another flow control hub that can be used with the drug delivery system of FIG. 1.

In some embodiments, the flow restriction introduced by flow control hub 16 may be performed using a single adjustable flow restrictor. For example, FIG. 5 is a schematic diagram of another flow control hub 200 that may be used with drug delivery system 10 that includes inlet connector 30 and outlet connectors 32A and 32B, which are substantially the same as those described above. Flow control hub 200 also includes a single flow restrictor 202 that impedes the flow to both outlet connectors 32A and 32B, and an optional adjustment mechanism 204 that controls the location of the fluid flow from inlet connector 30 through flow restrictor 202.

Flow restrictor 202 may include a sintered metal powder or sintered polymer powder such that depending on where the fluid entry point is along flow restrictor 202 (demonstrated by the arrows in FIG. 5) will determine how flow restrictor 202 divides the fluid flowing to the plurality of outlet connectors 32A and 32B based on the selected flow distribution. The amount of restriction introduced by flow restrictor 202 may depend on the porosity and the length of travel through the restrictor. In such systems, flow restrictor 202 functions similar to a potentiometer to distribute the fluid flow through flow control hub 200 by setting the relative travel lengths from the entry point of the restrictor to the respective outlet points.

In some embodiments, adjustment mechanism 204 may be adjusted and set by the physician during implantation to adjust the relative length of the flow path through flow restrictor 202 to the respective outlet connectors 32A and 32B. Additionally, or alternatively, adjustment mechanism 204 may be adjusted after implantation using, for example, a magnetic selector to set the positioning of adjustment mechanism 204 percutaneously. While adjustment mechanism 204 provides greater adjustment control within flow control hub 200, inclusion of adjustment mechanism 204 is optional. In other embodiments, the inlet position into flow restrictor 202 may be fixed at a specified flow distribution such as an equal split between outlet connectors 32A and 32B.

Figure 6:
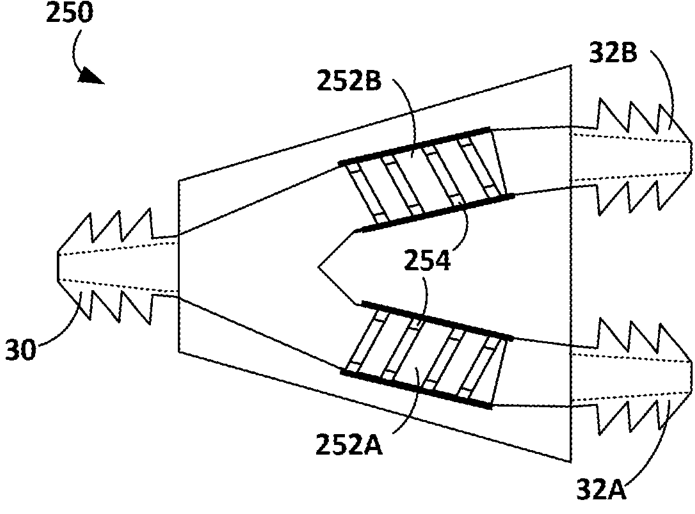
FIG. 6 is a schematic diagram of another flow control hub that can be used with the drug delivery system of FIG. 1.

FIG. 6 is a schematic diagram of another flow control hub 250 that may be used with drug delivery system 10 that includes inlet connector 30 and outlet connectors 32A and 32B, which are substantially the same as those described above. Flow control hub 250 also includes circuitous pathway flow restrictors 252A and 252B, each having a large length to width ratio. Flow restrictors 252A and 252B each include helical shape channels 254 etched into a central core material (e.g., sapphire chip, rigid polymer, metal, or the like). In some embodiments, the central core material may resemble a threaded rod with channel 254 representing the space between the threads. The central core material may be sheathed with a suitable material (e.g., polymeric tube or portions of hub material) to define the helical flow pathway there through. The flow resistance provided circuitous pathway by flow restrictors 252A and 252B may be varied by adjusting the overall length or cross-section of channels 254 based on Equation 1 to provide a five-fold or greater resistance to flow compared to the theoretical restriction produced by the catheter being coupled to the respective outlet connector 32A or 32B. In some embodiments, channels 254 may define a total flow length of about 1 cm to about 10 cm (e.g., about 2 cm to about 6 cm) for width on the order of about 0.13 mm. In some embodiments, circuitous pathway flow restrictors 252A and 252B may define a large flow length to width ratio on the order of about 10:1 to about 100:1.

Figure 7:
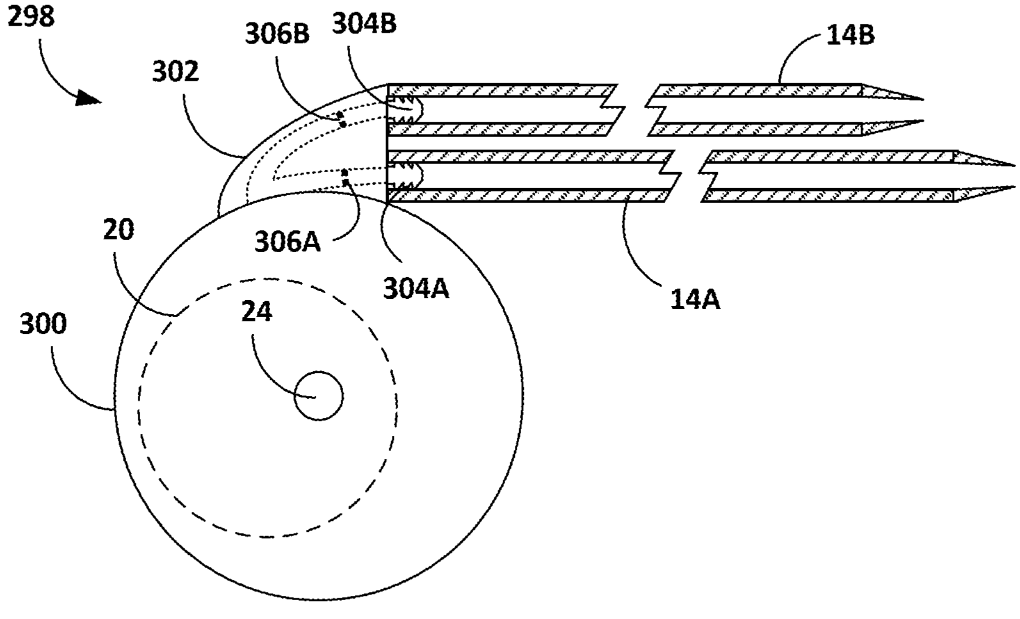
FIG. 7 is schematic diagram of another implantable drug delivery system in accordance with the disclosure.

In some embodiments, the function of flow control hub 16 may be incorporated into a portion of the drug delivery device. FIG. 7 is a schematic diagram of an example drug delivery system 298 including drug delivery device 300 (e.g., drug pump or drug port) that includes drug reservoir 20, optional access port 24, and header 302, with header 302 coupled to treatment catheters 14A and 14B. Drug reservoir 20, access port 24, and catheters 14A and 14B may be substantially the same as those described above with respect to FIG. 1. Header 302 includes a plurality of outlet connectors 304A and 304B, each being configured to attach to the proximal ends of catheters 14A and 14B respectively for the delivery of fluid containing one or more pharmaceutical agents to target treatment sites.

As shown in FIG. 7, drug delivery device 300 includes a split flow pathway between drug reservoir 20 and catheter connectors 304A and 304B. The forked pathway is shown as a bifurcated pathway within header 302 but may occur elsewhere within drug delivery device 302 or include more than two flow pathways.

The device also includes one or more flow restrictors shown as flow restrictors 306A and 306B which may be substantially similar to flow restrictors 18A, 18B, 252A, or 252B. As discussed above, flow restrictors 306A and 306B regulate the fluid flow distribution within catheters 14A and 14B due to the predominate pressure drop created by the respective restrictor compared to other portions of the distal flow path to the target treatment sites. Alternatively, drug delivery device 300 may include a flow restrictor substantially similar to flow restrictor 202 with optional adjustment mechanism 204. By including one or more flow restrictors similar to those described above within drug delivery device 300, the device can be used with conventional catheters and implantation techniques while still obtaining a highly regulated fluid flow profile.

The disclosed drug delivery system 10 may be used to treat various neurological diseases; examples are chronic pain, chronic pain, tremors, Parkinson's disease, cancer, epilepsy, urinary or fecal incontinence, sexual dysfunction, obesity, spasticity, gastroparesis, or other disorders. Various types of pharmaceutical agents may be used for the treatment of such diseases. Examples of possible pharmaceutical agents that can be used with system 10 include, but are not limited to, one or more of Gabapentin, Baclofen, Midazolam, or Valproate Na for the treatment of epilepsy; insulin for the treatment of diabetes, analgesics for pain management; and the like. For effective delivery, the distal ends of catheters 14A and 14B may be positioned within the CSF, portions of the brain, other areas of the body, or combinations thereof.

FIG. 8 is a flow diagram of a method of implanting and using drug delivery system 10 for the treatment of one or more medical conditions. The method depicted in FIG. 8 includes implanting a plurality of treatment catheters 14A and 14B within the body of a patient so that the distal end of each catheter is implanted at a respective treatment site (400), coupling a proximal end of each treatment catheter 14A and 14B to a respective outlet connector 32A, 32B, 304A, or 304B on either flow control hub 16 or 200 containing one or more flow restrictors or on drug delivery device 298 containing one or more flow restrictors configured to provide a selected flow distribution to treatment catheters 14A and 14B (402); and administering a fluid containing one or more pharmaceutical agents using the drug delivery device through the treatment catheters 14A and 14B to the target treatment sites, in which the fluid is distributed under the selected flow distribution (204).

As discussed above, implanting plurality of treatment catheters 14A and 14B (400) may be performed using the aid of a guide member (e.g., guidewire or guide catheter). The guide member may be introduced through at least a portion of the body of the patient to the target treatment site. A respective treatment catheter 14A or 14B may then be navigated to the respective target treatment site using the guide member followed by removal of the guide member prior to coupling the treatment catheter to the flow control hub or drug delivery device.

The method of FIG. 8 also includes coupling a proximal end of each treatment catheter 14A and 14B to a respective outlet connector 32A, 32B, 304A, or 304B on either flow control hub 16 or 200 or on drug delivery device 298 (402). Depending on which is used, the respective flow control hub or drug delivery device will include one or more of the above described flow restrictors 18A, 18B, 202, 252A, 252B, 306A, or 306B configured to impede the flow of the fluid containing the one or more pharmaceutical agents to the plurality of outlet connectors 32A, 32B, 304A, or 304B in order to regulate the flow of the fluid through the plurality of treatment catheters 14A and 14B.

In examples where flow control hub 16 or 200 is used, the flow control hub can be fluidically connected to the drug delivery device (e.g., drug pump or drug port). In such examples, the drug delivery device may include a new device implanted with flow control hub 16 or 200 or can include preexisting devices that are retrofitted with flow control hub 16 or 200.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An implantable drug delivery system configured to deliver one or more pharmaceutical agents to two or more treatment sites within a body of a patient, the system comprising:

a drug delivery device configured to deliver a fluid at a total volumetric flow rate, the fluid comprising the one or more pharmaceutical agents;

a plurality of treatment catheters configured to be implanted within the body of a patient and transport the fluid to the two or more treatment sites; and a flow control hub configured to passively control and passively regulate a flow of the fluid under a selected flow distribution that divides the total volumetric flow rate of the fluid between the plurality of treatment catheters, each treatment catheter receiving a sub-portion of the total volumetric flow rate, the flow control hub comprising:

an inlet connector that fluidically connects to the drug delivery device to receive the fluid;

a plurality of outlet connectors that each couple to a respective catheter of the plurality of treatment catheters;

a single flow restrictor sized and positioned within a respective fluid pathway from the inlet connector to a respective outlet connector of the plurality of outlet connectors, the single flow restrictor providing a fixed flow restriction that is set before, during or after the system is implanted within the body of the patient and thereafter provides a fixed flow resistance that passively controls the flow of the fluid from the inlet connector to the plurality of outlet connectors and the plurality of treatment catheters under the selected flow distribution and thereby passively regulates and manages fluid flow through the treatment catheters to provide controlled flow rates and a controlled fluid distribution within the plurality of treatment catheters when using the drug delivery device due to a predominate pressure drop created by the single flow restrictor compared to pressure drops along the respective fluid pathway distal to the fixed flow restriction; and an adjustment mechanism that controls a location of the fluid flowing from the inlet connector through the single flow restrictor to set the selected flow distribution, wherein the adjustment mechanism is configured to be magnetically adjusted percutaneously after implantation to adjust the selected flow distribution, wherein a ratio of the sub-portions of the total volumetric flow rate flowing through the plurality of treatment catheters is determined by the selected flow distribution of the single flow restrictor within the respective fluid pathways.

2. The drug delivery system of claim 1, wherein the drug delivery device comprises a drug pump comprising:

a drug reservoir for receiving the one or more pharmaceutical agents;

a header comprising an outlet connector that fluidically connects to the inlet connector of the flow control hub; and a pump mechanism configured to pump the fluid comprising the one or more pharmaceutical agents from the drug reservoir through the outlet connector; and an optional access port disposed on an exterior housing of the drug pump, the access port comprising a self-sealing septum that enables a needle to access the drug reservoir percutaneously.

3. The drug delivery system of claim 2, further comprising an intermediate catheter having a proximal end that couples to the outlet connector of the drug delivery device and a distal end that couples to the inlet connector of the flow control hub.

4. The drug delivery system of claim 2, wherein the outlet connector of the drug delivery device couples to the inlet connector of the flow control hub.

5. The drug delivery system of claim 1, wherein the single flow restrictor comprise a sintered metal, a sintered polymer, a capillary tube, an orifice, circuitous pathway, or a combination thereof.

6. The drug delivery system of claim 1, wherein the pressure drop across the single flow restrictor is about 2 to about 10 psi for a flow rate of about 10 microliters/minute.

7. The drug delivery system of claim 1, wherein the single flow restrictor provides a theoretical flow resistance of at least 5 times greater than a theoretical flow resistance of each catheter of the plurality of catheters.

8. The drug delivery system of claim 1, wherein the single flow restrictor is the same to provide a substantially equal fluid flow distribution to the plurality of treatment catheters.

9. An implantable drug delivery system configured to deliver one or more pharmaceutical agents to two or more treatment sites within a body of a patient, the system comprising:

a plurality of treatment catheters configured to be implanted within the body of a patient and transport one or more pharmaceuticals agent to two or more treatment sites; and a drug delivery device configured to deliver a fluid comprising the one or more pharmaceutical agents to the patient through the plurality of treatment catheters, the drug delivery device delivering the fluid at a total volumetric flow rate, the drug delivery device comprising:

a drug reservoir for receiving the one or more pharmaceutical agents;

a header configured to passively control and passively regulate a flow of the fluid under a selected flow distribution that divides the total volumetric flow rate of the fluid between the plurality of treatment catheters, each treatment catheter receiving a sub-portion of the total volumetric flow rate, the header comprising a plurality of outlet connectors that each couple to a respective catheter of the plurality of treatment catheters;

a pump mechanism configured to pump the fluid comprising the one or more pharmaceutical agents from the drug reservoir through the outlet connectors; and a single flow restrictor sized and positioned within a respective fluid pathway from an inlet connector to a respective outlet connector of the plurality of outlet connectors, the single flow restrictor providing a fixed flow restriction that is set before, during or after the system is implanted within the body of the patient and thereafter provides a fixed flow resistance that passively controls the flow of the fluid from the drug reservoir to the plurality of outlet connectors and the plurality of treatment catheters under the selected flow distribution and thereby passively regulates and manages fluid flow through the treatment catheters to provide controlled flow rates and a controlled fluid distribution within the plurality of treatment catheters when using the drug delivery device due to a predominate pressure drop created by the single flow restrictor compared to pressure drops along the respective fluid pathway distal to the fixed flow restriction; and wherein the drug delivery device further comprises an adjustment mechanism that controls a location of the fluid flowing from the drug reservoir through the single flow restrictor to set the selected flow distribution, wherein a ratio of the sub-portions of the total volumetric flow rate flowing through the plurality of treatment catheters is determined by the selected flow distribution of the single flow restrictor within the respective fluid pathways.

10. The implantable drug delivery system of claim 1, wherein the drug delivery device further comprises an access port disposed on an exterior housing of the drug delivery device, the access port comprising a self-sealing septum that enables a needle to access the drug reservoir percutaneously.

11. The drug delivery system of claim 9, wherein the pressure drop across the single flow restrictor is about 2 to about 10 psi for a flow rate of about 10 microliters/minute.

12. The drug delivery system of claim 9, wherein the single flow restrictor provides a theoretical flow resistance of at least 5 times greater than a theoretical flow resistance of each catheter of the plurality of catheters.

13. The drug delivery system of claim 9, wherein the single flow restrictor comprises a sintered metal powder or sintered polymer powder.

14. An implantable medical device comprising:

a flow control hub configured to passively control and passively regulate a flow of fluid under a selected flow distribution, comprising:

an inlet connector configured to fluidically connect to a drug delivery device that delivers a fluid comprising one or more pharmaceutical agents to the inlet connector, the fluid being delivered at a total volumetric flow rate;

a plurality of outlet connectors each configured to fluidically connect to a respective treatment catheter; and a single flow restrictor sized and positioned within a respective fluid pathway from the inlet connector to a respective outlet connector of the plurality of outlet connectors, the single flow restrictor providing a fixed flow restriction that is set before, during or after implantation of the hub within a body of a patient and thereafter provides a fixed flow resistance that passively controls the flow of the fluid from the inlet connector to the plurality of outlet connectors and the plurality of outlet connectors under the selected flow distribution and thereby passively regulates and manages fluid flow through the treatment catheters to provide controlled flow rates and a controlled fluid distribution within the plurality of treatment catheters when using the drug delivery device due to a predominate pressure drop created by the single flow restrictor compared to pressure drops along the respective fluid pathway distal to the fixed flow restriction; and an adjustment mechanism that controls a location of the fluid flowing from the inlet connector through the single flow restrictor to set the selected flow distribution, wherein the adjustment mechanism is configured to be magnetically adjusted percutaneously after implantation to adjust the selected flow distribution, wherein the selected flow distribution divides the total volumetric flow rate of the fluid between the plurality of outlet connectors, each outlet connector receiving a sub-portion of the total volumetric flow rate, and wherein a ratio of the sub-portions of the total volumetric flow rate flowing through the plurality of outlet connectors is determined by the selected flow distribution of the single flow restrictor within the respective fluid pathways.

15. The implantable medical device of claim 14, wherein the single flow restrictor comprise a sintered metal, a sintered polymer, a capillary tube, an orifice, a circuitous pathway, or a combination thereof.

16. The implantable medical device of claim 14, wherein the pressure drop across the single flow restrictor is about 2 to about 10 psi for a flow rate of about 10 microliters/minute.

17. The implantable medical device of claim 14, wherein the fixed flow restriction is set before implantation.

18. The implantable medical device of claim 14, wherein the fixed flow restriction is set during or after implantation.

19. The drug delivery system of claim 9, wherein the fixed flow restriction is set before implantation.

20. The drug delivery system of claim 9, wherein the fixed flow restriction is set during or after implantation.

21. The drug delivery system of claim 1, wherein the fixed flow restriction is set before implantation.

22. The drug delivery system of claim 1, wherein the fixed flow restriction is set during or after implantation.

23. The drug delivery system of claim 1, wherein the ratio comprises an unequal distribution of the total volumetric flow rate between the plurality of treatment catheters.

24. The drug delivery system of claim 1, wherein the ratio comprises a 40:60, 30:70, or 20:80 distribution of the total volumetric flow rate between the plurality of treatment catheters.

25. The implantable medical device of claim 14, wherein the ratio comprises an unequal distribution of the total volumetric flow rate between the plurality of outlet connectors.

* * * * *